United States Patent [19]

Sweet

[11] 3,959,325

[45] May 25, 1976

[54] COPPER II SALT OF 4-CHLOROPHTHALIC ACID

[75] Inventor: Ronald L. Sweet, Westfield, N.J.

[73] Assignee: E. I. du Pont De Nemours and Company, Wilmington, Del.

[22] Filed: Sept. 23, 1974

[21] Appl. No.: 508,653

[52] U.S. Cl. ............................................ 260/438.1
[51] Int. Cl.² ......................................... C07F 1/08
[58] Field of Search ................................ 260/438.1

[56] References Cited
UNITED STATES PATENTS

| | | | |
|---|---|---|---|
| 2,769,731 | 11/1956 | Schneid et al. | 260/438.1 X |
| 2,799,594 | 7/1957 | Ehrich | 106/288 |
| 2,805,957 | 9/1957 | Ehrich | 106/288 |
| 3,354,191 | 11/1967 | Stivers | 260/438.1 X |
| 3,717,493 | 2/1973 | Griswold | 106/288 Q |

OTHER PUBLICATIONS

Chemical Abstracts, 54, 5123a (1960).

*Primary Examiner*—Helen M. S. Sneed

[57] ABSTRACT

The copper II salt of 4-chlorophthalic acid prepared by reacting 4-chlorophthalic acid or a monoalkali metal salt thereof with copper II ion in aqueous solution under conditions of controlled pH. The copper II salt of 4-chlorophthalic acid is useful as an intermediate in the preparation of chlorine-containing copper phthalocyanine pigment.

5 Claims, No Drawings

COPPER II SALT OF 4-CHLOROPHTHALIC ACID

BACKGROUND OF THE INVENTION

It is well known in the art, e.g., Ehrich U.S. Pat. No. 2,799,594, that incorporation of chlorine in copper phthalocyanine pigment inhibits the tendency of this pigment to grow crystals and thus lose tinctorial strength in many hydrocarbon solvents in which it is used. The principal method of manufacture of phthalocyanine pigments containing chlorine is by adding a mono-alkali metal salt of 4-chlorophthalic acid or, less commonly, the free acid to a conventional synthetic mixture containing phthalic anhydride, anhydrous cupric chloride, urea, and a catalyst such as ammonium molybdate in a saturated hydrocarbon solvent. The alkali salt of 4-chlorophthalic acid is conventionally prepared by chlorination of phthalic anhydride in a caustic aqueous solution. The resulting precipitate of the alkali salt of 4-chlorophthalic acid is isolated by filtration, and thereafter is added to the phthalocyanine synthesis reaction medium.

Problems exist in the isolation and subsequent use of the alkali salts of 4-chlorophthalic acid because they are quite soluble in water, to the extent that a saturated aqueous solution of the mono-sodium salt of 4-chlorophthalic acid contains about 9 ½% by weight and that of the mono-potassium salt, 5%. Because of the high solubility of these salts, the usual practice prior to filtration has been to "salt out" the alkali metal salt of 4-chlorophthalic acid by addition of large amounts of inorganic salts such as sodium chloride and potassium chloride. After filtration, the 4-chlorophthalic salt may then be washed with brine to remove impurities or may be pulled down without washing after which the filter-cake may be dried. During the filtration, with or without washing, appreciable amounts of the 4-chlorophthalic salt are lost in the filtrate. In addition, the filter-cake contains large amounts, e.g., up to 40% by weight on a dry basis, of sodium or potassium chloride, which are subsequently introduced into the phthalocyanine synthesis along with the alkali salt of 4-chlorophthalic acid.

When the phthalocyanine pigment is synthesized in a solvent medium, e.g., saturated aliphatic hydrocarbons or halogen-substituted aromatics, a common method for isolation of the pigment after the synthesis is to contact the pigment slurry with concentrated sulfuric acid whereby the pigment is transferred from the hydrocarbon solvent to the sulfuric acid. The solvent layer can then be separated by decantation and the acid layer can be drowned in water to precipitate the phthalocyanine. When the isolation procedure utilizes an amount of sulfuric acid which is insufficient to completely dissolve the phthalocyanine, as described in Ehrich U.S. Pat. No. 2,805,957, subsequent drowning results in the recovery of a crude phthalocyanine which requires further processing, e.g. grinding or ball milling, to produce a product of optimum pigmentary quality, i.e., small particle size. To obviate the need for further processing a commonly utilized method, described in Griswold U.S. Pat. No. 3,717,493, employs excess sulfuric acid to insure complete solution of the phthalocyanine and the formation of a pigmentary product upon drowning the acid solution into water.

In both procedures, the chloride salts, carried through from the isolation of the mono-alkali salt of 4-chlorophthalic acid, react with the sulfuric acid to liberate hydrogen chloride gas, which must be neutralized prior to disposal. In the procedure where large amounts of sulfuric acid are used, the amount of hydrogen chloride evolved is quite large, resulting in the consumption of large amounts of sulfuric acid and generation of a severe foaming problem. The foaming, which results from gas evolution, can create serious difficulties, particularly from the standpoint of ease of pigment processing. In addition, the quantity of gas evolved imposes a heavy burden on pollution control systems, such as scrubbing systems, making effluent purification more difficult and costly.

This invention provides for a compound to be used in place of 4-chlorophthalic acid and its alkali metal salts which substantially eliminates loss of intermediate and eliminates evolution of hydrogen chloride gas.

SUMMARY OF THE INVENTION

According to the invention there is provided the copper II salt of 4-chlorophthalic acid of the formula

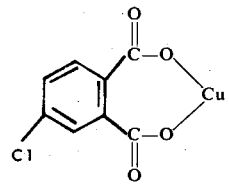

The copper II salt of 4-chlorophthalic acid is prepared by reacting 4-chlorophthalic acid or the mono-alkali metal salts thereof with a source of copper II ion in an aqueous medium at a pH between about 3.3 and 4.3. The structural formula is in accordance with conventional structures of divalent metal salts of a dibasic acid. However, since it is recognized that polymeric forms of such salts may exist, both wholly or partially polymerized forms of the salt are included in this invention where they exist.

The 4-chlorophthalic acid used in the preparation of the copper salt of the invention can be prepared by any of the well-known methods described in the literature, e.g., T. S. Moore et al., J. Chem. Soc., 119, 1786–91 (1921) and Bansho et al., Tokyo Kogyo Sh. Kensk. Hokoku 56 (4), 158–64 (1961), Chemical Abstracts 62:1609$^d$. The mono-alkali metal salts of 4-chlorophthalic acid used in the preparation of the copper salt of the invention is commonly prepared by the method described by T. S. Moore et al., op. cit. The source of copper II ion can be any inorganic salt of copper II, e.g., copper sulfate, cupric chloride, cupric bromide and cupric acetate or mixtures thereof, which is soluble in aqueous media and which does not interfere with the formation of the copper II salt of 4-chlorophthalic acid and any excess of which can easily be separated from the copper II salt of 4-chlorophthalic acid prior to reaction with phthalic anhydride in the subsequent synthesis of chlorine-containing copper phthalocyanine.

The relative quantities of 4-chlorophthalic acid or its salts and source of copper II ion used in the process of the invention are not particularly critical. However, it is desirable to use a moderate excess of the source of copper II ion, e.g., 5–20% in excess of that required to react stoichiometrically, to insure complete reaction of the 4-chlorophthalic acid or its salts.

DETAILED DESCRIPTION OF THE INVENTION

Although acceptable product can be obtained in the pH range of 3.3 to 4.3, the preferred reaction pH range is about 3.4 to 3.5 to insure the greatest yield of the copper II salt of 4-chlorophthalic acid. Appreciable deviation from this pH range substantially depresses the recovery of the copper II salt. In the case of pH above about 4.3, precipitation of the copper hydroxide takes place thus contaminating any copper II salt of 4-chlorophthalic acid which may form at that pH and considerably reduces the yield of copper II salt.

The copper II salt of 4-chlorophthalic acid which precipitates from the aqueous reaction medium can be isolated by filtration and washed free of any contaminants with water, without significant loss of product, because the solubility of the copper II salt of 4-chlorophthalic acid is only to the extent of 0.095% by weight in a saturated aqueous solution at 25°C. The resulting filter cake can then be dried or, alternatively, can be dewatered by topping water off in the solvent medium used for the subsequent synthesis of the copper phthalocyanine. Since there is no need to add inorganic salts, e.g., potassium or sodium chloride, in order to precipitate the copper II salt of 4-chlorophthalic acid, the isolated product contains no additional salt to form hydrogen chloride gas upon reaction with the acid used in subsequent steps of copper phthalocyanine isolation. In addition, the copper II ion from the copper II salt of the invention is subsequently utilized as a source of copper in the copper phthalocyanine synthesis.

The copper II salt of 4-chlorophthalic acid can be added alone or with acid to the reaction medium for the synthesis of copper phthalocyanine. In order to insure a uniform distribution of the 4-chlorophthalic acid in the synthesis slurry and to obtain a smooth reaction, it is generally preferred that some acid be added to the synthesis slurry. For this purpose any strong mineral acid, e.g., HC1, strong organic acid, e.g., p-toluenesulfonic acid, or acid-reacting salt, e.g., ammonium chloride, can be used.

In order to describe more completely and specifically the process of this invention, the following examples are given. Parts and percentages therein are by weight unless otherwise specified.

EXAMPLE 1

Preparation of Copper II Salt of 4-chlorophthalic Acid from 4-chlorophthalic acid The 4-chlorophthalic acid anhydride is prepared by the well-known procedure described in T. S. Moore et al., J. Chem. Soc., 119, 1786–91 (1921). The anhydride is isolated by distillation according to the procedure described in Bansho et al., Tokyo Kogyo Sh. Kensk. Hokoku 56 (4) 158–64 (1961), Chemical Abstracts 62:1609$^d$, after which the anhydride is hydrolyzed to the acid. The resulting 4-chlorophthalic acid has a melting point of 148°C. and is found by analysis to have a chlorine content of 18.0%, compared to the calculated value of 17.7%.

To a solution of 4.01 parts of the above-prepared 4chlorophthalic acid in 50 parts of water is added 6.0 parts of $CuSO_4.5H_2O$ in 50 parts of water. The pH of the resulting solution is adjusted to 3.45 by addition of NaOH. The precipitated product is stirred for 4 hours at 50°C. After cooling the product slurry to room temperature, the product is isolated by filtration, washed with water to 6000 ohms resistivity, and dried. 5.02 parts (97% yield) of the copper II salt of 4-chlorophthalic acid is recovered.

The copper II salt is analyzed and found to contain 22.0% Cu and 13.5% C1, compared to calculated values of 24.2% Cu and 13.53% C1. The X-ray diffraction pattern exhibits a principal interplanar spacing of 14.5A and very much smaller interplanar spacings of 7.0A, 4.8A, 4.6A, 3.9A and 2.7A.

EXAMPLE 2

Preparation of Copper II Salt of 4-Chlorophthalic Acid from the Sodium Salt of 4-Chlorophthalic Acid To 53 parts of water is added 11.8 parts of a 50% aqueous solution of sodium hydroxide, after which 5.5 parts of phthalic anhydride is added. The solution is stirred for 15 minutes and cooled to between 6°C and 10°C. Over a period of 4 hours, 7 parts of chlorine gas is added to the solution. The resulting solution is stirred for 30 minutes, after which the pH is between about 4.4 and 4.7. Over a period of 1 hour, 3.6 parts of 98% sulfuric acid is added and the solution is stirred for 3 more hours. At the end of this period, the pH of the solution is about 2.0.

To the above-prepared mixture of the sodium salt of 4-chlorophthalic acid is added 6.5 parts of copper sulfate pentahydrate ($CuSO_4.5H_2O$). The solution is stirred for 60 minutes to insure complete solution of the $CuSO_4.5H_2O$. The pH of the resulting solution is adjusted to between 3.40 and 3.45 with sodium hydroxide solution and the solution is stirred for 30 minutes. The copper II salt of 4-chlorophthalic acid which precipitates from the above solution is isolated by filtration and washed with water to a resistivity of 600 ohms.

The copper II salt is analyzed and found to exhibit substantially the same X-ray diffraction pattern as the copper II salt of Example I.

EXAMPLE 3

Preparation of Pigmentary Chlorinated Copper Phthalocyanine from the Copper II Salt of 4Chlorophthalic Acid and Phthalic Anhydride The copper II salt of 4-chlorophthalic acid prepared in Example 2 is added in the form of a wet press cake to 45.5 parts of deodorized kerosene. The resulting slurry is dewatered by topping off the water at a temperature of 110°C. To the resulting dewatered slurry is added 110 parts of deodorized kerosene, .05 parts of dibutyl p-cresol, 40 parts of urea, 2.13 parts of cuprous chloride, 0.18 parts of molybdenum oxide ($MoO_3$), 21 parts phthalic anhydride and 1.25 parts of ammonium chloride. The slurry is then heated to 200°C. over a period of 4 ½ hours and held at the temperature for 2 hours. The slurry is cooled to 30°C., after which the crude halogenated copper phthalocyanine pigment formed therein is flushed from the reaction medium into 223 parts of 98% sulfuric acid. The resulting solution of phthalocyanine pigment in sulfuric acid is then drowned in water under high turbulence to precipitate the halogenated copper phthalocyanine pigment in pigmentary form, essentially all of which is in the α I phase.

The pigment is conditioned by heating in perchloroethylene in the presence of a quaternary ammonium surfactant according to the procedure described in Griswold U.S. Pat. No. 3,717,493. After removal of the perchloroethylene solvent, the pigment is recovered by filtration and washing. The purified pigment is analyzed and found to contain 3.9% chlorine.

EXAMPLE 4

Preparation of a Crude Chlorinated Copper Phthalocyanine from the Copper II salt of 4-chlorophthalic acid and Phthalic Anhydride The following ingredients are charged to a well-agitated reactor equipped with a reflux condenser and external heating:

|  | Parts |
| --- | --- |
| Copper II salt of 4-chlorophthalic acid | 7.49 |
| Phthalic anhydride | 22 |
| Urea | 40 |
| Copper I chloride | 2.04 |
| Molybdenum oxide | 0.12 |
| Ammonium chloride | 1.19 |
| Deodorized kerosene | 156 |

The mixture is heated under nitrogen to 195°C. over a period of three hours and held at 195°C. with good agitation for two hours. After cooling the mixture to 90°C., 77 parts of 98% $H_2SO_4$ is added slowly. The mixture is then stirred for 5 minutes and allowed to settle for 30 minutes. The kerosene layer is removed from the highly viscous $H_2SO_4$ layer by decantation, after which the $H_2SO_4$ layer is added to 1000 g. of ice and diluted to 2000 cc. with water. The resulting aqueous slurry is heated to 95°C. and held at this temperature for 15 minutes. The pH of the slurry is adjusted to 10.5–11.5 by addition of NaOH and heated to 90-95°C. while stirring for two hours. The resulting product is isolated by filtration, washed free of soluble salts with water, and dried at 120°C. under vacuum. The yield of chlorinated copper phthalocyanine crude is 22.6 parts. The crude product is purified by conventional techniques and the purified sample is found by analysis to contain 3.64% Cl.

What is claimed is:
1. The copper II salt of 4-chlorophthalic acid.
2. Process for the preparation of the copper II salt of 4-chlorophthalic acid by reacting in aqueous medium at a pH from 3.3 to 4.3 at least one compound selected from the group consisting of 4-chlorophthalic acid and a monoalkali metal salt of 4-chlorophthalic acid with a source of copper II ion.
3. Process according to claim 2 wherein said pH is between about 3.4 and 3.5.
4. Process according to claim 2 wherein said source of copper II ion is a water-soluble inorganic salt of copper II.
5. Process according to claim 4 wherein said inorganic salt of copper II is $CuSO_4.5H_2O$.

* * * * *